(12) United States Patent
Hung et al.

(10) Patent No.: US 11,045,805 B2
(45) Date of Patent: Jun. 29, 2021

(54) MICROFLUIDIC SYSTEM AND METHOD FOR ARRANGING OBJECTS

(71) Applicant: Bio-Rad Laboratories, Inc., Hercules, CA (US)

(72) Inventors: Lung-Hsin Hung, Arlington, MA (US); Robert Meltzer, Belmont, MA (US); Lucas Frenz, San Leandro, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 279 days.

(21) Appl. No.: 16/178,300

(22) Filed: Nov. 1, 2018

(65) Prior Publication Data

US 2019/0126277 A1    May 2, 2019

Related U.S. Application Data

(60) Provisional application No. 62/580,338, filed on Nov. 1, 2017.

(51) Int. Cl.
*B01L 3/00* (2006.01)
*C12Q 1/6869* (2018.01)

(52) U.S. Cl.
CPC ... *B01L 3/502761* (2013.01); *B01L 3/502784* (2013.01); *C12Q 1/6869* (2013.01);
(Continued)

(58) Field of Classification Search
CPC ..... B01L 2200/0647; B01L 2200/0673; B01L 2200/143; B01L 2400/0487;
(Continued)

(56) References Cited

U.S. PATENT DOCUMENTS

| 4,676,898 A | 6/1987 | Saxena |
| 6,797,056 B2 | 9/2004 | David |

(Continued)

FOREIGN PATENT DOCUMENTS

| WO | 2007011622 A2 | 1/2007 |
| WO | 2012081983 A1 | 6/2012 |

OTHER PUBLICATIONS

Copenheaver, Blaine R., Authorized Officer, ISA/US, Commissioner for Patents, "International Search Report" in connection with related International Application No. PCT/US2018/058778, dated Feb. 7, 2019, 2 pgs.

(Continued)

*Primary Examiner* — Maureen Wallenhorst
(74) *Attorney, Agent, or Firm* — Kolisch Hartwell, P.C.

(57) ABSTRACT

Microfluidic systems and methods for arranging a set of objects. In an exemplary method, the set of objects may be transported in carrier fluid along a microfluidic channel structure having a reformatting zone including an object-accessible region and at least one object-excluding region. A portion of the carrier fluid may be moved from the object-accessible region to the at least one object-excluding region in an upstream section of the reformatting zone, to reduce a spacing of objects of the set. The portion of the carrier fluid may be directed into the object-accessible region from the at least one object-excluding region in a downstream section of the reformatting zone, to increase a spacing of objects of the set. The steps of moving and directing in combination may increase the spacing between objects disproportionately for a subset of the objects that are closest to one another.

19 Claims, 9 Drawing Sheets

(52) U.S. Cl.
CPC . *B01L 3/502776* (2013.01); *B01L 2200/0647* (2013.01); *B01L 2200/0673* (2013.01); *B01L 2200/143* (2013.01); *B01L 2400/0487* (2013.01); *Y10T 436/2575* (2015.01)

(58) Field of Classification Search
CPC ......... B01L 3/502761; B01L 3/502776; B01L 3/502784; C12Q 1/6869; Y10T 436/25; Y10T 436/2575
USPC .... 436/63, 165, 174, 180; 422/82.05, 82.09, 422/502, 503, 504, 505
See application file for complete search history.

(56) References Cited

U.S. PATENT DOCUMENTS

| | | | |
|---|---|---|---|
| 7,294,503 | B2 | 11/2007 | Quake et al. |
| 7,641,862 | B2 | 1/2010 | Noetzel et al. |
| 8,241,571 | B2 | 8/2012 | Goix et al. |
| 9,132,394 | B2 | 9/2015 | Makarewicz, Jr. et al. |
| 2006/0072177 | A1 | 4/2006 | Putnam et al. |
| 2008/0003142 | A1 | 1/2008 | Link et al. |
| 2008/0014589 | A1 | 1/2008 | Link et al. |
| 2009/0014360 | A1 | 1/2009 | Toner et al. |
| 2009/0056116 | A1 | 3/2009 | Presley et al. |
| 2010/0015606 | A1 | 1/2010 | Davies et al. |
| 2010/0078077 | A1* | 4/2010 | Ismagilov ......... B01L 3/502784 137/1 |
| 2011/0311978 | A1 | 12/2011 | Makarewicz, Jr. et al. |
| 2012/0108721 | A1 | 5/2012 | Mazutis |
| 2012/0190033 | A1 | 7/2012 | Ness et al. |
| 2013/0295568 | A1 | 11/2013 | Link |
| 2014/0045712 | A1 | 2/2014 | Link et al. |
| 2014/0071452 | A1 | 3/2014 | Fleischer |
| 2014/0170736 | A1 | 6/2014 | Heredia et al. |
| 2014/0200164 | A1 | 7/2014 | Makarewicz, Jr. et al. |
| 2014/0202546 | A1* | 7/2014 | Ismagilov ............. B01F 5/0471 137/1 |
| 2014/0221239 | A1 | 8/2014 | Carman et al. |
| 2015/0065396 | A1 | 3/2015 | Kiani et al. |
| 2016/0051958 | A1* | 2/2016 | Kung ................... B01J 19/0046 506/26 |
| 2016/0171686 | A1 | 6/2016 | Du et al. |
| 2016/0257992 | A1 | 9/2016 | Tsukuda |
| 2017/0007998 | A1 | 1/2017 | Fraden et al. |
| 2017/0183722 | A1 | 6/2017 | Link |
| 2019/0002956 | A1 | 1/2019 | Stumbo et al. |
| 2020/0108393 | A1* | 4/2020 | Lee ................... B01L 3/502746 |

OTHER PUBLICATIONS

Copenheaver, Blaine R., Authorized Officer, ISA/US, Commissioner for Patents, "Written Opinion of the International Searching Authority" in connection with related International Application No. PCT/US2018/058778, dated Feb. 7, 2019, 14 pgs.

\* cited by examiner

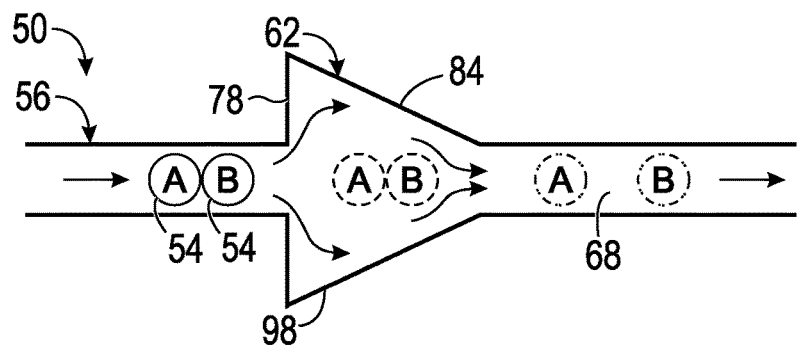
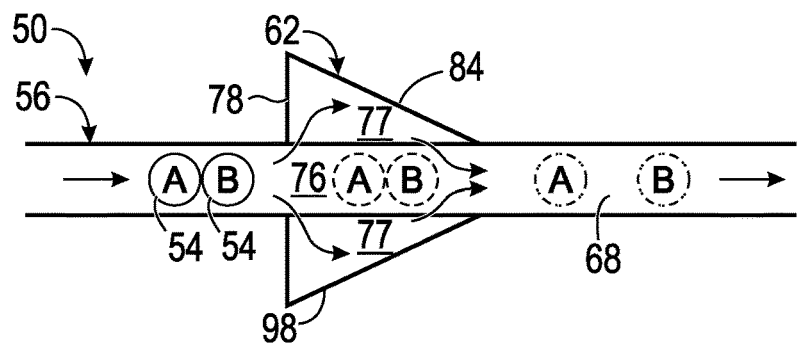
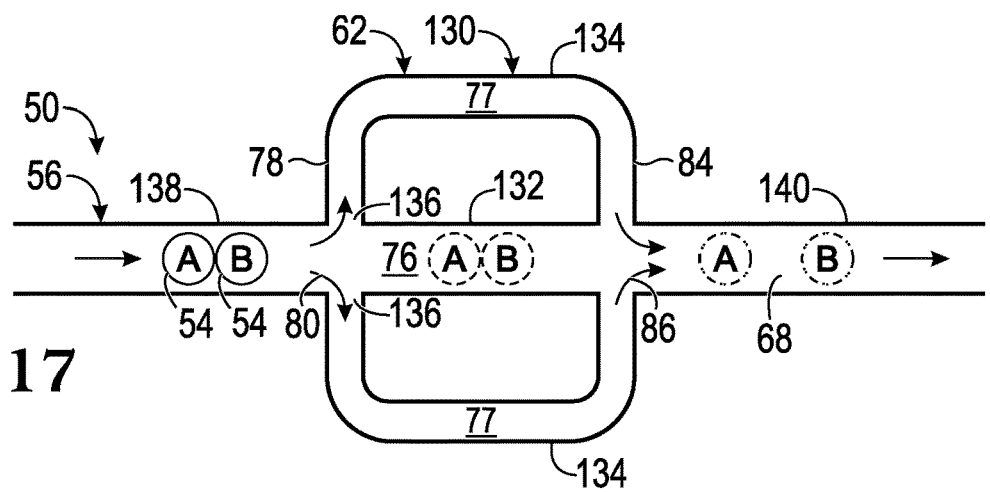
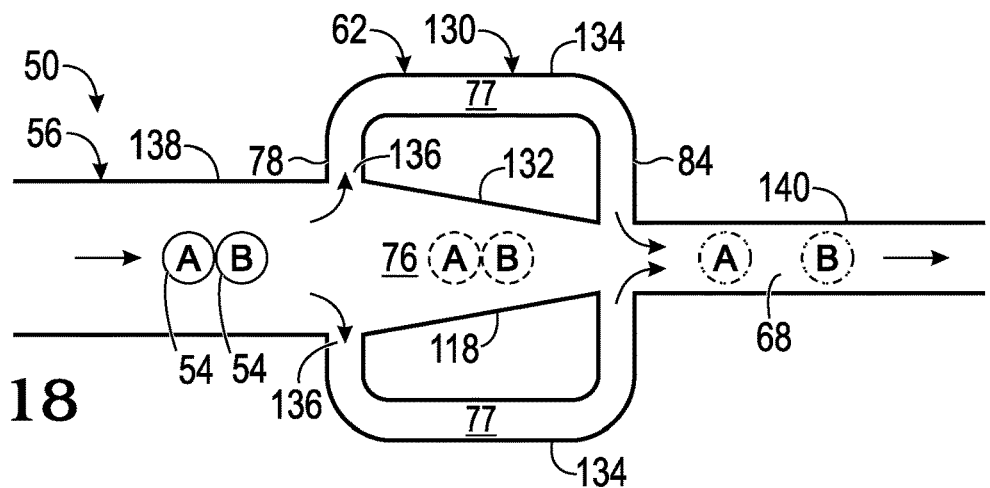

MICROFLUIDIC SYSTEM AND METHOD FOR ARRANGING OBJECTS

CROSS-REFERENCE TO PRIORITY APPLICATION

This application is based upon and claims the benefit under 35 U.S.C. § 119(e) of U.S. Provisional Patent Application Ser. No. 62/580,338, filed Nov. 1, 2017, which is incorporated herein by reference in its entirety for all purposes.

INTRODUCTION

Microscopic objects, such as beads, cells, or droplets, can be arranged in a stream by a microfluidic system to enable detection or further manipulation for an assay. However, the spacing of objects within the stream is usually stochastic. As a result, some of the objects may be in very close proximity to one another, which can make the assay more difficult to perform and may introduce error into assay results.

SUMMARY

The present disclosure provides microfluidic systems and methods for arranging a set of objects. In an exemplary method, the set of objects may be transported in carrier fluid along a microfluidic channel structure having a reformatting zone including an object-accessible region and at least one object-excluding region. A portion of the carrier fluid may be moved from the object-accessible region to the at least one object-excluding region in an upstream section of the reformatting zone, to reduce a spacing of objects of the set. The portion of the carrier fluid may be directed into the object-accessible region from the at least one object-excluding region in a downstream section of the reformatting zone, to increase a spacing of objects of the set. The steps of moving and directing in combination may increase the spacing between objects disproportionately for a subset of the objects that are closest to one another. The method may produce a more uniform spacing of objects and/or a lower incidence of objects in close proximity to one another.

BRIEF DESCRIPTION OF THE DRAWINGS

FIG. 15 is a view of an exemplary tapered geometry for the reformatting zone of the microfluidic system of FIG. 1, with the reformatting zone having a uniform depth (and no object-excluding region), in accordance with aspects of the present disclosure.

FIG. 16 is a view of another exemplary tapered geometry for the reformatting zone of the microfluidic system of FIG. 1, with the reformatting zone having object-excluding regions of reduced depth to receive carrier fluid while restricting lateral travel of the objects, in accordance with aspects of the present disclosure.

FIG. 17 is a view of an exemplary branched geometry for the reformatting zone of the microfluidic system of FIG. 1, with the reformatting zone having a primary channel and a pair of lateral by-pass channels that branch from the primary channel upstream and rejoin the primary channel downstream, in accordance with aspects of the present disclosure.

FIG. 18 is a view of another exemplary branched geometry for the reformatting zone of the microfluidic system of FIG. 1, with the reformatting zone being similar to that of FIG. 17, except having a primary channel that tapers in the reformatting zone to place objects in single file, in accordance with aspects of the present disclosure.

DETAILED DESCRIPTION

Figure 1:
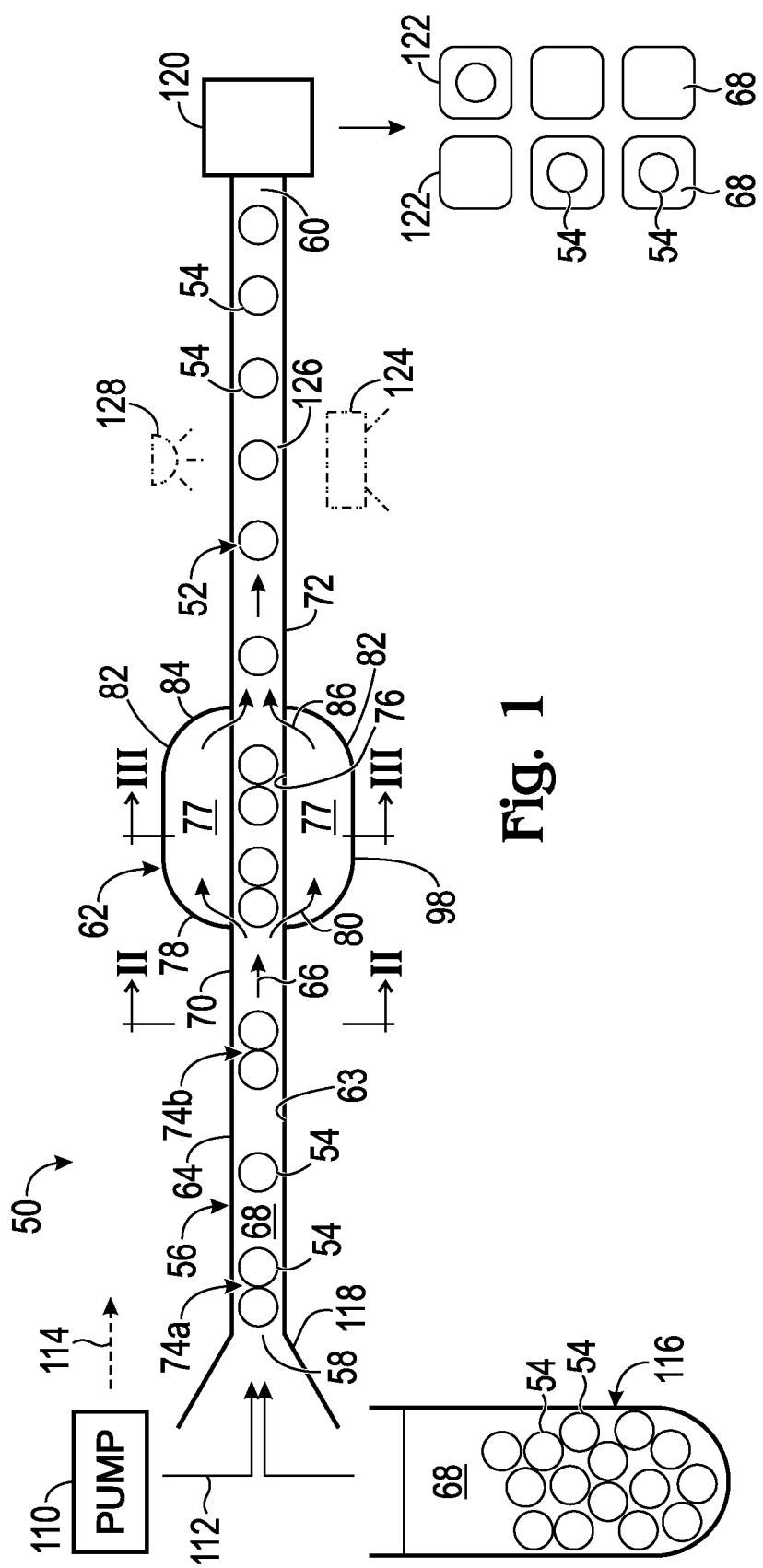
FIG. 1 is a schematic view of an exemplary microfluidic system for arranging objects, in accordance with aspects of the present disclosure.

The present disclosure provides microfluidic systems and methods for arranging a set of objects. In an exemplary method, the set of objects may be transported in carrier fluid along a microfluidic channel structure having a reformatting zone including an object-accessible region and at least one object-excluding region. A portion of the carrier fluid may be moved from the object-accessible region to the at least one object-excluding region in an upstream section of the reformatting zone, to reduce a spacing of objects of the set. The portion of the carrier fluid may be directed into the object-accessible region from the at least one object-excluding region in a downstream section of the reformatting zone, to increase a spacing of objects of the set. The steps of moving and directing in combination may increase the spacing between objects disproportionately for a subset of the objects that are closest to one another. The method may produce a more uniform spacing of objects and/or a lower incidence of objects in close proximity to one another.

The present disclosure provides an exemplary method of altering the spacing of a stream of objects. The stream of objects may be transported in carrier fluid along a microfluidic channel structure defining an object-excluding flow path for the objects and having a reformatting zone including an upstream section and a downstream section. A portion of the carrier fluid may be moved out of the flow path in the upstream section such that objects within the stream move closer to one another. The portion of the carrier fluid may be directed into the flow path in the downstream section to increase a distance between objects within the stream. The stream may have a more uniform spacing of the objects downstream of the downstream section compared to upstream of the upstream section, and/or a lower incidence of objects in close proximity to one another downstream relative to upstream of the reformatting zone.

The general concept is to have a stream of carrier fluid (e.g., a liquid stream) flowing in a microfluidic channel and carrying objects (e.g. droplets, particles, etc.). The objects may have a size in the same range as a transverse dimension of the microfluidic channel (e.g., 1-500 micrometers). Various exemplary microfluidic designs are disclosed which alter the spacing between these objects within the channel. An exemplary purpose is to reduce the likelihood of two adjacent objects traveling in close proximity to one another in the stream of carrier fluid, and/or to render the spacing of the objects more uniform within the stream of carrier fluid. Close proximity may be defined as a percentage of the average spacing between objects, such as less than 100%, 80% 60%, 50%, 40%, 30%, 25%, 20%, or 10% of the average spacing.

Altering the spacing of the objects could be beneficial for various applications. For example, the application could be spacing of a fluorescent readout from the objects. Other applications involve partitioning a liquid stream carrying the objects. For example, if the liquid stream is to be partitioned into a plurality of isolated (separate) fluid volumes, there is a certain probability (typically, a Poisson distribution) that a given number of objects (i.e., 0, 1, 2, 3, etc.) will end up in the same fluid volume. By altering the spacing of the objects, and particularly objects that are in close proximity to one another, the probability of having two objects very close to one another can be reduced. As a result, the altered spacing creates a lower probability of having two or more objects within the same fluid volume. Essentially, this may overcome an underlying Poisson probability.

Exemplary microfluidic channel structures disclosed herein may utilize a similar concept. In these designs, a portion of the carrier fluid may be drained away from the objects by moving the portion to one or more object-excluding regions of the channel structure. This movement of carrier fluid concentrates objects within an object-accessible region of the channel structure. Objects that are farther apart get closer to one another. Objects that already are close to one another may get even closer. However, since the objects have a finite size, there is a physical limit to how closely the centers of the objects can approach one another before further approach is mutually obstructed. Accordingly, the objects may be concentrated differentially, with a subset of the objects that are closest together being concentrated less than objects that are farther apart. The portion of carrier fluid may be reintroduced into the object-accessible region of the channel structure, thereby diluting objects within the channel to increase the spacing thereof. The objects may be diluted equally. Therefore, the spacing between a subset of the objects, namely, each adjacent pair of objects that exhibited mutual obstruction during concentration, may be increased disproportionately by concentration and dilution. Furthermore, concentrating and diluting objects may create a larger minimum spacing between the objects. The minimum spacing may be determined by the size of the objects and the amount of carrier fluid that was drained from and reintroduced into the channel. The minimum spacing between objects before concentration may be about the same as the diameter of the objects. The minimum spacing after dilution may be at least about 125%, 150%, 175%, 200%, or 250%, among others, of the diameter of the objects. The minimum spacing between objects may be increased at least 25%, 50%, 75%, 100%, or 150%, among others, by concentration and dilution.

Further aspects of the present disclosure are described in the following sections: (I) definitions, (II) overview of microfluidic systems and methods for arranging objects, (III) reformatting zones, and (IV) examples.

I. Definitions

Technical terms used in this disclosure have meanings that are commonly recognized by those skilled in the art. However, the following terms may be further defined as described below.

Object—any entity having a diameter of less than one millimeter. The objects of a set or object stream may have any suitable diameter, such less than 500, 200, or 100 micrometers and/or greater than 1, 2, 5, 10, or 20 micrometers, among others. In exemplary embodiments, the objects may have a width of 1-500 micrometers, 5-500 micrometers, 10-200 micrometers, or the like. The objects of a set or object stream may be about the same size. For example, the objects may have a standard deviation of their respective diameters that is less than about 40%, 30%, 20%, 15%, or 10% of the mean of the diameters. A "stream" of objects may be a substantially single-file arrangement of the objects, whether or not the objects are exactly aligned with one another along a flow axis. Accordingly, the objects of an object stream may be offset somewhat from one another laterally, such as offset from a flow axis by less than about 75%, 50%, or 25% of the diameter of the objects. An object stream interchangeably may be described as a line, train, succession, or series of objects.

The objects may have any suitable shape. The objects of a set or line may or may not be rounded and/or elongated. The present disclosure utilizes spherical objects to illustrate the systems and methods, and the term "diameter" to describe the width of the objects. However, the term "diameter" is intended to mean width (e.g., an average width) for any shape of object.

The objects may be composed of matter having any suitable state, such as solid, liquid, gas, or a combination thereof. However, the objects may be predominantly solid, predominantly liquid, and/or predominantly a combination of solid and liquid, in some embodiments. The objects may be substantially incompressible and/or rigid when subjected to the microfluidic manipulations disclosed herein. Exemplary objects include particles, droplets, and the like. The particles may be biological cells or beads, among others. The droplets may be composed at least predominantly of liquid.

Spacing—a distance between an adjacent pair of objects, a set of individual distances between adjacent objects of a group, object stream, or set, or an average distance between adjacent objects of a group, object stream, or set. The distance (a center-to-center spacing) between an adjacent pair of objects may be measured from the center of one of the objects to the center of the other object. This distance may be described as a separation or separation distance between the objects, whether or not there is any space between the objects.

Microfluidic—involving fluid manipulation on a sub-millimeter scale. For example, a microfluidic channel may have a characteristic dimension, such as a width or depth, of less than one millimeter. Microfluidic systems, and channels thereof, may produce and guide a laminar flow of fluid, and/or may operate with a Reynolds number of less than about 500, 200, 100, or 50, among others.

Carrier fluid—a fluid in which objects are transported in a microfluidic system, channel structure, and/or channel. The carrier fluid may be liquid. In some embodiments, the carrier fluid may be aqueous (or may be non-aqueous). The carrier fluid may be immiscible with liquid of the objects, if the objects include liquid. If the objects are solid, the objects may be substantially insoluble in the carrier fluid. In some embodiments, the carrier fluid may comprise oil, and the objects may be aqueous droplets, or the carrier fluid may be aqueous, and the objects may be droplets comprising oil, among others.

Channel—an elongated, fluid-guiding structure. A channel may be enclosed radially along most or all of its longitudinal extent.

Channel structure—a fluid-guiding structure including a single channel or two or more channels that communicate with one another. The channel structure may be unbranched or branched. Each of the channels may be a microfluidic channel. The channel structure may be configured to guide fluid from an inlet to an outlet, without any substantial addition or loss of fluid. The channel structure may have a cross-sectional area for fluid flow at each position between the inlet and the outlet. The cross-sectional area may be defined at each position by a single channel, or collectively by two or more channels configured to carry fluid in parallel.

II. Overview of Microfluidic Systems and Methods for Arranging Objects

This section provides an overview of exemplary microfluidic systems and methods for arranging objects; see FIGS. 1-10.

FIG. 1 shows a schematic view of an exemplary microfluidic system 50 for arranging objects, and particularly for reformatting a stream 52 of objects 54 to space the objects more uniformly. The system includes a channel structure 56 having an inlet 58 (e.g., a single inlet), an outlet 60 (e.g., a single outlet), and a reformatting zone 62 located on an object-accessible flow path 63 that connects the inlet to the outlet. The channel structure may have only one channel 64 extending between the inlet and outlet and forming the reformatting zone, as in the depicted embodiment. In other embodiments, channel structure 56 may branch upstream and merge downstream to create the reformatting zone (see Section II).

Channel structure 56 may be configured to direct a stream 66 of carrier fluid 68 transporting objects 54 from inlet 58 to outlet 60, with the objects following, and substantially restricted to, flow path 63. The objects may be arranged in object stream 52, which may be straight, bent, curved, or the like. In other embodiments described below, the objects may be placed into single file by the reformatting zone, and thus the objects may enter the reformatting zone laterally spread out.

Reformatting zone 62 may have a fixed geometry that passively (e.g., without valves, feedback, electrical signals, etc.) adjusts the spacing between at least a subset of the objects, to make the spacing less stochastic (such as to make the spacing less of a Poisson distribution). For example, in the depicted embodiment, objects 54 located upstream of reformatting zone 62 in an inflow region 70 of the channel structure have a more variable spacing than objects 54 located downstream of reformatting zone 62 in an outflow region 72 of the channel structure. More particularly, inflow region 70 contains two unseparated pairs 74a, 74b of objects, while all of objects 54 in outflow region 72 are well separated from one another. As described further below, the reformatting zone may be configured to disproportionately increase the relative and/or absolute spacing between adjacent objects that are spaced from one another by less than a threshold distance.

Reformatting zone 62 may be configured to concentrate and dilute objects, to produce a change in the spacing between the objects. The zone may have an object-accessible region 76 (e.g., the part of flow path 63 passing through zone 62) in which objects 54 can travel, and one or more object-excluding regions 77 that selectively and/or substantially exclusively permit entry of carrier fluid 68 relative to objects 54. Object-excluding regions 77 may be configured to exclude a majority of the objects from entering the region, such as more than about 70%, 80%, 90%, 95,%, 98% or 99% of the objects, among others.

Reformatting zone 62 may have a concentration section 78, interchangeably called an upstream section, in which a portion of carrier fluid 68 is moved from flow path 63, indicated by arrows at 80. The portion of carrier fluid is moved from object-accessible region 76 to object-excluding regions 77. The portion of carrier fluid may be moved into one or more wings 82 (i.e., one or more lateral areas) of channel 64 (and/or into one or more by-pass channels) that branch from the channel and are separate from one another.

Reformatting zone 62 also may have a dilution section 84, interchangeably called a downstream section or re-entry section, in which the portion of carrier fluid 68 may be reintroduced into flow path 63 (and thus into object-accessible region 76) from object-excluding regions 77 (e.g., from one or more wings 82), indicated by arrows at 86. The velocity of objects 54 may (or may not) decrease in concentration section 78, and/or carrier fluid may be drained from the object-accessible region of the reformatting zone, which may cause objects 54 to be concentrated locally. The local spacing of objects 54 in the reformatting zone may decrease, relative to their spacing in inflow region 70. The velocity of objects 54 may increase, and/or carrier fluid 68 may be reintroduced into object-accessible region 76 in dilution section 84, which may cause the spacing between objects 54, such as the spacing for each adjacent pair 74a, 74b, to be increased from the more concentrated configuration in the reformatting zone.

Reformatting zone 62 may have any suitable length. For example, the length may be at least about 2, 3, 4, 5, 10, or 20 object diameters, among others.

Figure 2:
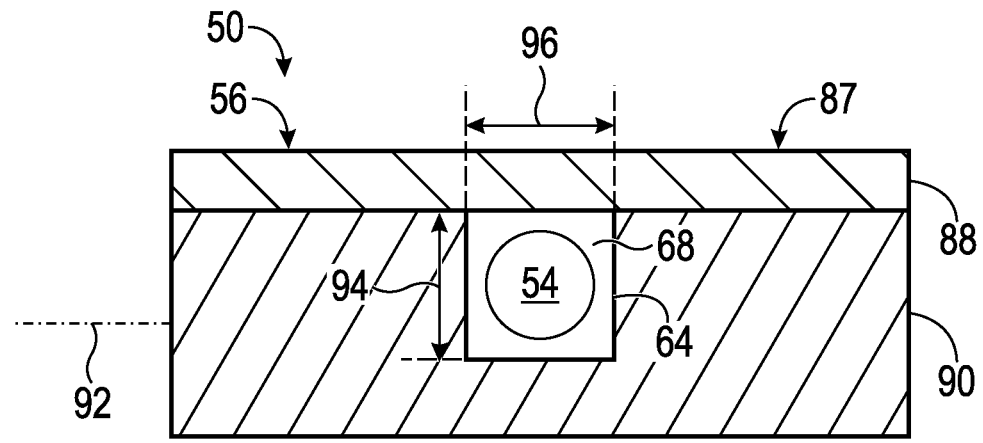
FIG. 2 is a sectional view of the microfluidic system of FIG. 1, taken generally along line II-II of FIG. 1 at a position upstream of a reformatting zone of the system.

FIG. 2 shows an exemplary geometry for channel structure 56 upstream (and/or downstream) of reformatting zone 62. The channel structure may be formed by a channel-defining device 87 having a plurality of layers, such as layers 88, 90, bonded to one another and defining a plane 92. Channel 64, in inflow region 70, and/or outflow region 72, may be sized in correspondence with objects 54 (see FIGS. 1 and 2). The channel may have a depth 94 (measured orthogonal to plane 92) and a width 96 (measured parallel to plane 92) that are about the same as one another, such as less than about 100%, 75%, 50%, or 25% different. The size of channel 64 in inflow region 70 and outflow region 72 may be the same, or may be different. For example, the outflow region may have a smaller cross-sectional area, depth, and/or width than the inflow region (also see below). The depth and/or width of the outflow region and/or inflow region may be only somewhat larger than the diameter of objects 54, such as less than about 100%, 75%, 50%, or 25% larger, among others, to reduce lateral migration of the objects out of alignment with one another.

Figure 3:
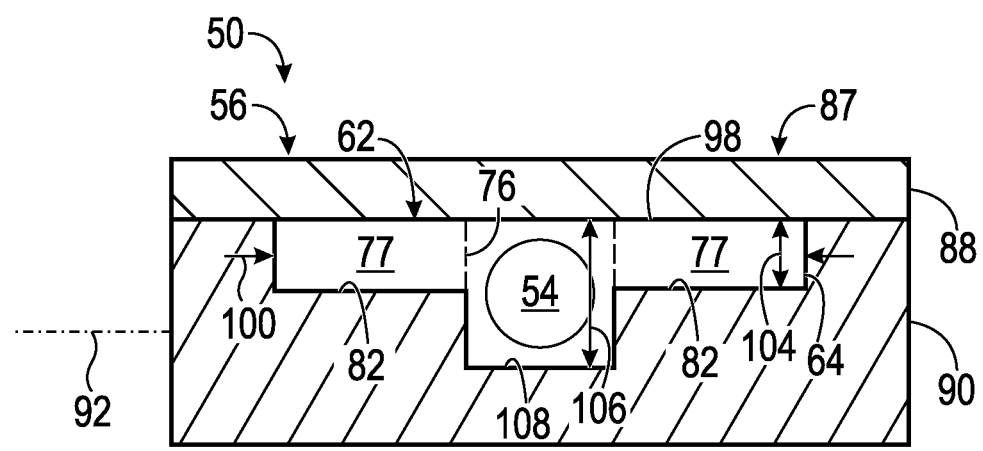
FIG. 3 is another sectional view of the microfluidic system of FIG. 1, taken generally along line III-III of FIG. 1 at a position intersecting the reformatting zone of the system.

FIG. 3 shows an exemplary geometry for channel structure 56 within reformatting zone 62. Channel 64 may (or may not) have an expanded region 98 (also see FIG. 1) at which a width 100 of the channel increases relative to width 96 of inflow region 70 and/or outflow region 72. Whether or not the channel has an expanded region, a depth 104 of object-excluding region(s) 77 (e.g., depth 104 of each wing 82) may be less than a depth 106 of object-accessible region 76, to form a shelf on one or both sides of object-accessible region 76. Depth 104 of each object-excluding region 77 may be less than the diameter of objects 54, to substantially exclude objects 54 from the object-excluding region. Accordingly, each object-excluding region 77 may be configured to permit selective movement of only carrier fluid 68, and not objects 54, from object-accessible region 76, making the process of draining carrier fluid from around objects 54 more efficient. Each object-excluding region 77 may have a substantially uniform depth, or the depth may vary stepwise or via a taper, among others, within the object-excluding region. Object-excluding regions 77 of FIGS. 1-3 and elsewhere herein are shown as being symmetrical, with object-accessible region 76 located between, contiguous with, and separating, a pair of object-excluding regions. However, in other embodiments, only a single object-excluding region 77 may be located on only one side of object-accessible region 76, the object-excluding regions may be asymmetrically arranged, or three or more object-excluding regions may be present.

Object-accessible region 76 may be formed adjacent each object-excluding region 77 at least in part by a groove 108. The object-accessible region may include laterally unbounded space above the groove, as indicated by a pair of dashed boundaries extending upward from the walls of the groove between wings 82.

The amount of increase and decrease in cross-sectional area of the channel structure created by expanded region 98 (and/or by one or more by-pass channels) may directly related to the fraction of carrier fluid that is drained from the object-accessible flow path and reintroduced to the flow path. Accordingly, a larger increase and decrease in cross-sectional area may provide a greater deceleration and acceleration of objects, and a larger effect on object spacing. The amount of increase in cross-sectional area may set a threshold separation distance between objects, below which the relative or absolute spacing within object pairs is increased disproportionately by the reformatting zone. With a smaller increase in cross-sectional area, the spacing between only closely paired objects may be affected disproportionately, while with a larger increase in cross-sectional area, the spacing within a greater percentage of the object pairs may be altered disproportionately.

FIG. 1 shows other exemplary aspects of system 50. One or more sources of positive/negative pressure, such as at least one pump 110, may be operatively connected to channel structure 56 upstream of inlet 58 and/or downstream of outlet 60. The pump(s) creates a pressure differential to move fluid within the channel structure. Each pressure source may be any device or mechanism configured to drive flow of carrier fluid 68 and objects 54 from inlet 58 to outlet 60. Each pump may, for example, apply positive pressure upstream of inlet 58, indicated at 112, to push carrier fluid, or may apply negative pressure (suction) downstream of outlet 60, indicated at 114, to pull carrier fluid. Exemplary pumps may include syringe pumps, peristaltic pumps, diaphragm pumps, piston pumps, and the like.

A source 116 of objects 54 and carrier fluid 68 may be connected to channel structure 56. Source 116 may be connected removably or integrally, among others. Objects 54 may be placed into single file as the objects enter channel structure 56. For example, the objects may travel through a tapered alignment region 118 leading to inlet 58. In other embodiments, alignment region 118 may be provided by reformatting zone 62 (see below).

System 50 may have a partitioning structure 120 located at or downstream of outlet 60. The partitioning structure may be configured to divide carrier fluid stream 66 into a plurality of isolated volumes 122 (interchangeably called partitions), optionally of equal size. The size of the volumes may be selected such that a majority of the volumes contain either no object 54 or only one object 54. Passing carrier fluid stream 66 through reformatting zone 62 before partitioning can make partitioning less random, by decreasing the percentage of volumes containing two or more objects 54 and increasing the percentage of volumes 122 containing only one object Partitioning structure 120 may have any suitable mechanism of operation. The partitioning structure may be a dispenser that dispenses volumes 122 into separate containers or as an aerosol. In other embodiments, the partitioning structure may form volumes 122 encapsulated by a continuous liquid phase. Accordingly, the partitioning structure may be a droplet generator. Exemplary droplet generators form droplets by flow focusing, shearing, co-flow, a confinement gradient, etc.

In some embodiments, system 50 may include a detector 124 operatively located downstream of reformatting zone 62. Detector 124 may be configured to detect a signal from a detection zone 126 of channel 64 as objects 54 pass therethrough. The reformatting zone increases the separation between closely paired objects and thus may reduce the incidence of signal overlap between detected waveforms corresponding to the objects. The detector may, for example, be configured to detect light from detection zone 126. In some embodiments, a light source 128 may be configured to irradiate the detection zone, such as to produce photoluminescence from the objects. The light source may provide epi- or trans-illumination of the detection zone. Partitioning structure 120 may or may not be omitted from embodiments including detector 124.

FIGS. 4-7 show part of channel structure 56 of system 50 of FIG. 1 in the presence of a pair of objects 54 ("A" and "B"). The upstream, center-to-center distance, spacing S1, between the objects in inflow region 70 is different in each figure to illustrate how reformatting zone 62 may operate on objects of different initial spacing. The same pair of objects 54 in each figure is shown as dashed inside reformatting zone 62, and in dash-dot-dot outline in outflow region 72 after passing through the reformatting zone. The spacing for the pair of objects at each of the three positions along the flow path is labeled as S1, S2, and S3, respectively. The changes in spacing shown in FIGS. 4-7 are exemplary; other channel geometries may produce larger or smaller changes. Furthermore, the reversible changes in separation shown in FIGS. 6 and 7 for S1 greater than the threshold distance may not apply in some case, such as if the cross-sectional areas of inflow region 70 and outflow region 72 are different.

Figure 4:
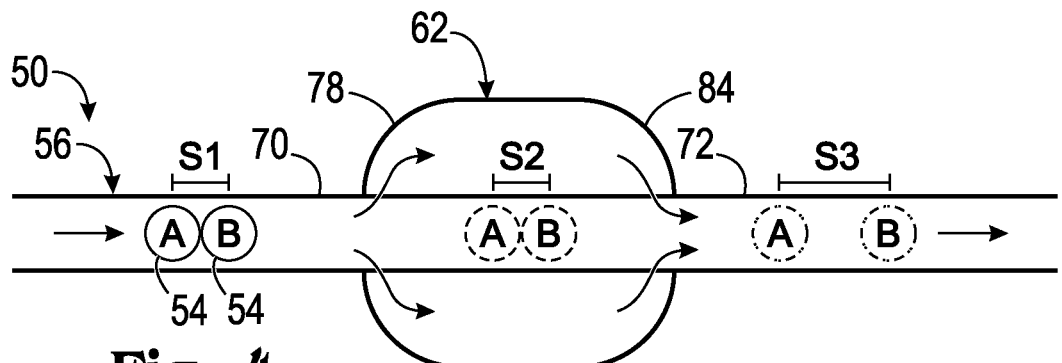
FIG. 4 is a fragmentary view of the system of FIG. 1 in the presence of a pair of objects ("A" and "B") that are in very close proximity to one another upstream of the reformatting zone and illustrating how the center-to-center distance (the spacing) between the objects may be changed by traveling through the reformatting zone of the system (compare spacing S1, spacing S2, and spacing S3).

FIG. 4 shows a configuration in which S1 is approximately equal to the diameter of the pair of objects. In other words, the objects are very close to one another before entering reformatting zone 62. Accordingly, although moving carrier fluid into object-excluding regions 77 in concentration section 78 urges the objects toward one another, the objects cannot move substantially closer to one another, and S1 substantially equals S2, because the objects mutually obstruct one another. However, the dilution produced by dilution section 84 causes the objects to move apart from one another, such that S3 is greater than S1 (and S2).

Figure 5:
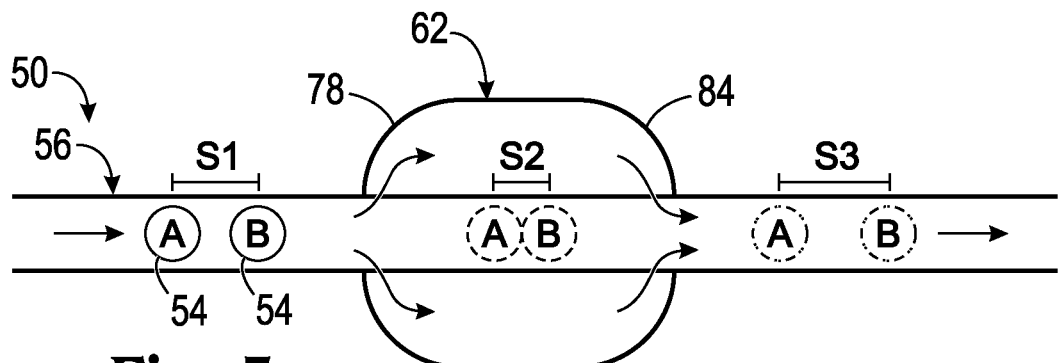
FIG. 5 is another fragmentary view of the system of FIG. 1, taken as in FIG. 4, except with the pair of objects farther apart than in FIG. 4 upstream of the reformatting zone.

FIG. 5 shows a configuration in which S1 is greater than in FIG. 4, but the two objects are still relatively close (e.g., S1 may be less than two object diameters). Moving carrier fluid into object-excluding regions 77 in concentration section 78 may urge the objects closer together until the objects mutually obstruct further movement toward one another. At this point, S2 is substantially equal to the diameter of the objects (i.e., S1), and no further movement toward each other is permitted without object deformation. As in FIG. 4, the dilution produced by dilution section 84 causes the objects to move apart from one another, such that S3 is greater than S1 (and S2). S3 in FIGS. 4 and 5 may be the same, since S2 is the same, even though S1 is different. Accordingly, each pair of objects having less than a threshold spacing for S1 may have the same spacing S3 as one another after passing through the reformatting zone. The threshold spacing may be determined by the diameter of the objects, and a ratio of the amount of concentration and the amount of dilution produced by the reformatting zone.

Figure 6:
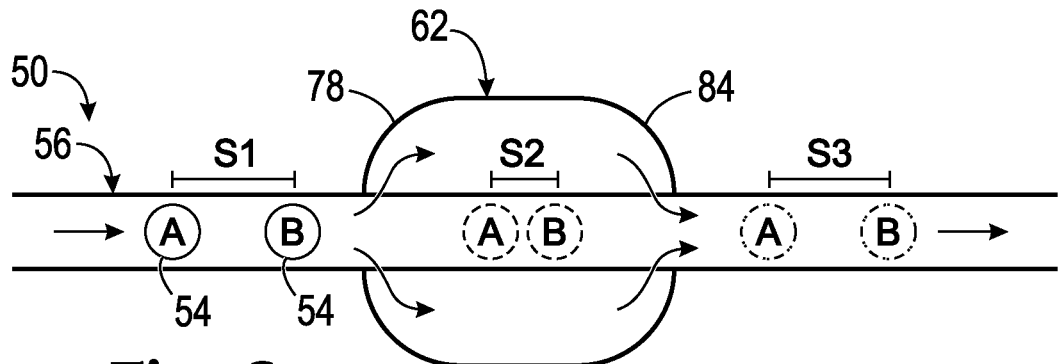
FIG. 6 is yet another fragmentary view of the system of FIG. 1, taken as in FIG. 4, except with the pair of objects farther apart than in FIG. 5 upstream of the reformatting zone.
Figure 7:
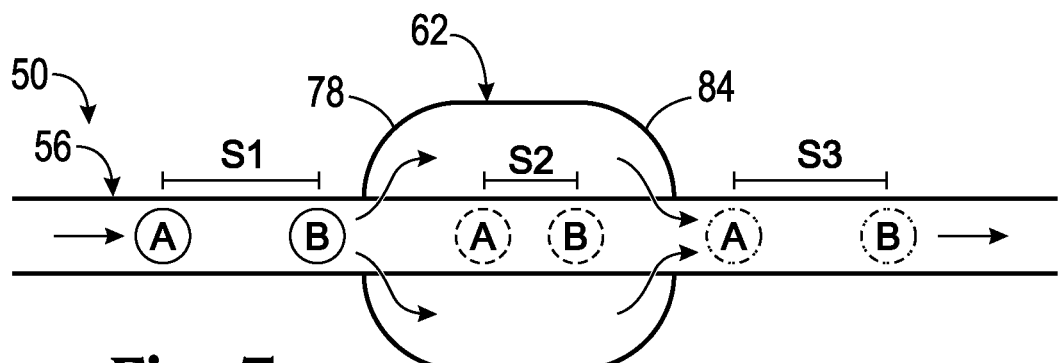
FIG. 7 is still another fragmentary view of the system of FIG. 1, taken as in FIG. 4, except with the pair of objects farther apart than in FIG. 6 upstream of the reformatting zone.

FIGS. 6 and 7 show configurations in which S1 is greater than in FIG. 5 (and greater than the threshold spacing). More particularly, S1 is large enough that moving carrier fluid into object-excluding regions 77 in concentration section 78 urges the objects closer together but not close enough for the objects to obstruct movement toward one another. Accordingly, the dilution produced by dilution section 84 causes the objects to move apart from one another to their original spacing (i.e., S1 equals S3). At the threshold spacing (e.g., intermediate S1 of FIGS. 5 and 6), the objects may move to the closest approach of FIGS. 4 and 5 but still may return to their original spacing. Any adjacent objects having less than the threshold spacing for S1 leave the reformatting zone with substantially the same spacing S3, which is the reformatted minimum spacing between objects.

Figure 8:
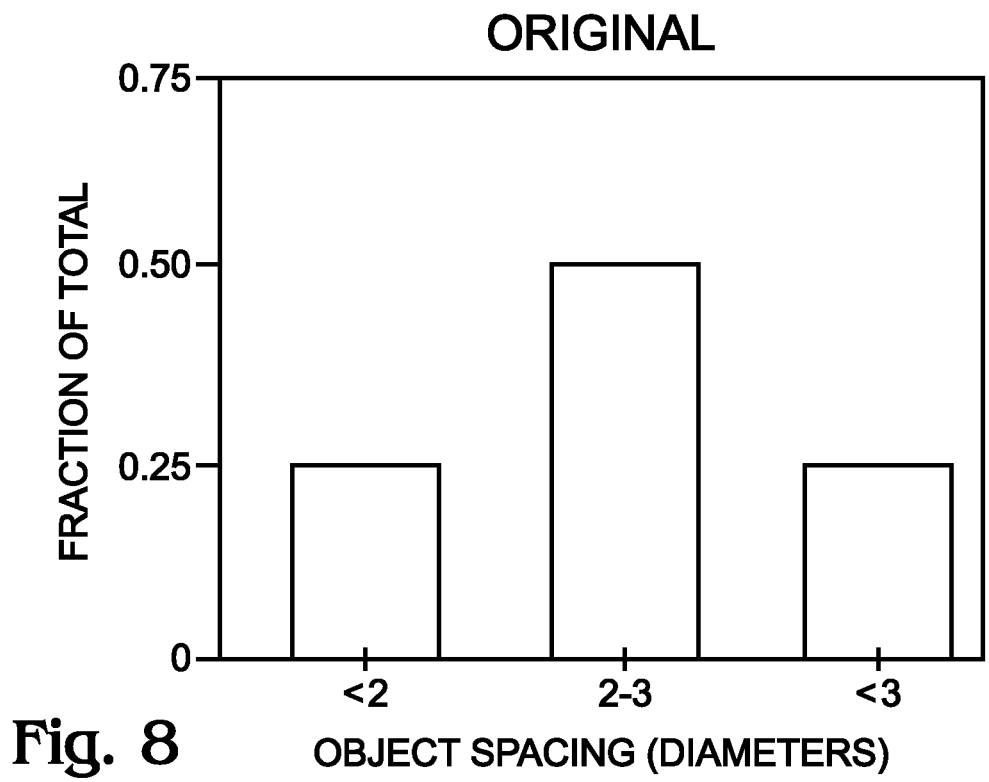
FIG. 8 is a histogram showing an exemplary distribution of the center-to-center distances (the spacing) between objects before the objects have been passed through the reformatting zone of the microfluidic system of FIG. 1, in accordance with aspects of the present disclosure.

FIG. 8 shows a histogram presenting an exemplary distribution of the spacing between objects 54 upstream of reformatting zone 62. Objects that are relatively closer together (e.g., represented by the bar on the left) may be undesirable for applications in which the objects should be well singulated.

Figure 9:
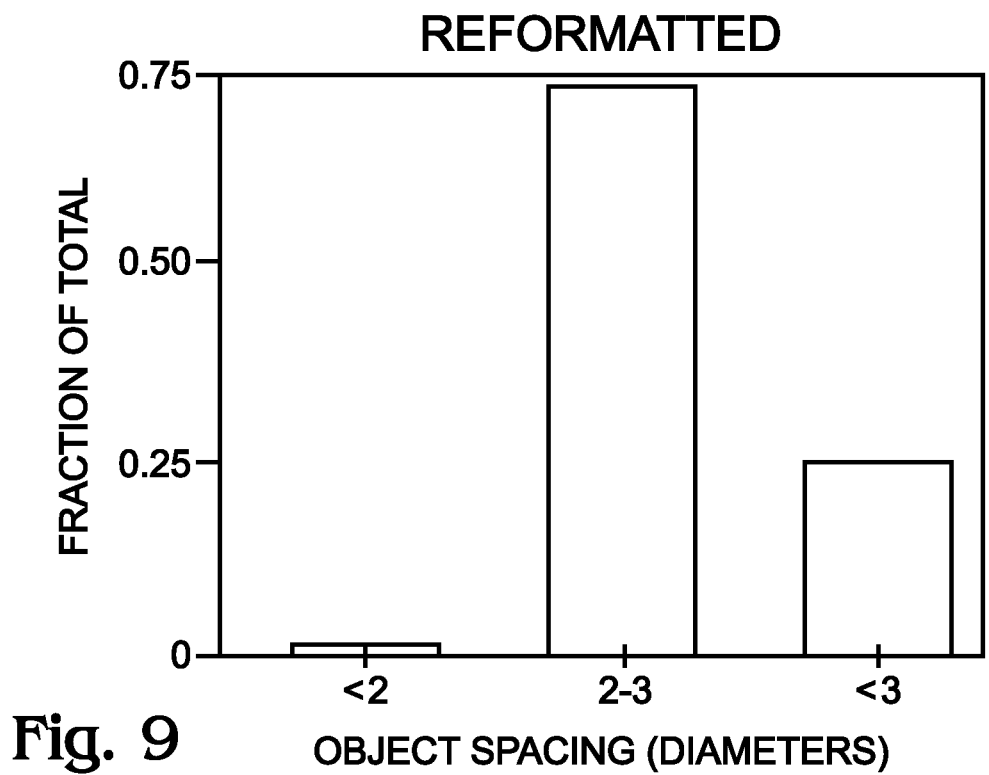
FIG. 9 is a histogram showing an exemplary distribution of the center-to-center distances (the spacing) between objects that were spaced originally as in FIG. 8, but after the objects have been passed through the reformatting zone of the microfluidic system of FIG. 1, in accordance with aspects of the present disclosure.

FIG. 9 shows a histogram presenting an exemplary change in the distribution of FIG. 8 produced by passing the objects through reformatting zone 62 of system 50. In FIG. 9, the threshold spacing for reformatting zone 62 (see FIGS. 5 and 6) is between two and three. Accordingly, the object pairs that were represented by the bar on the left (in FIG. 8) have been spaced farther from one another and are now represented by the middle bar of the histogram. However, the spacing of the rest of the object pairs may not have changed significantly. Accordingly, the spacing of the objects has been adjusted to increase the average distance between objects, by selectively (and/or disproportionately) increasing the spacing between a subset of the objects that are closest to one another.

Figure 10:
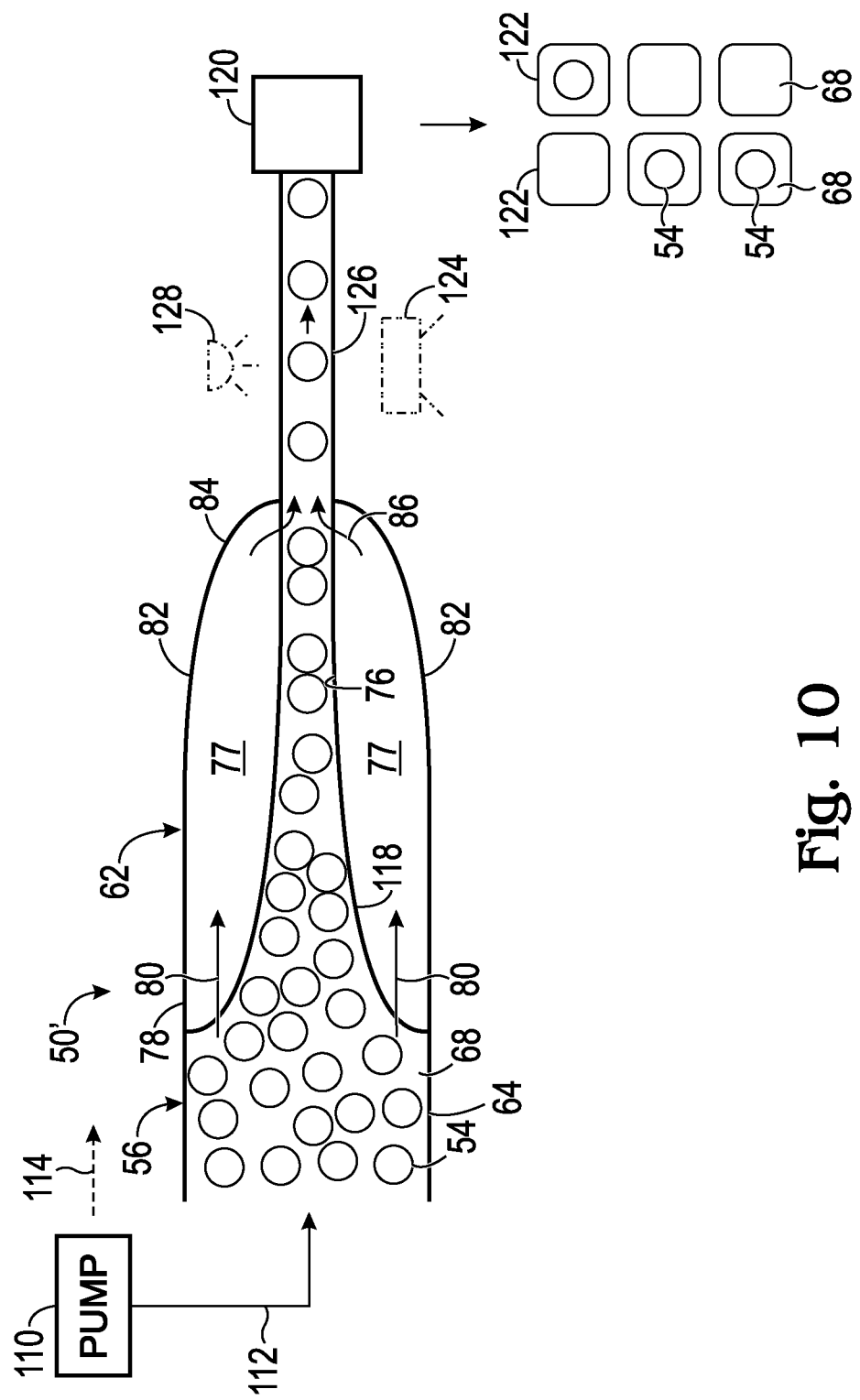
FIG. 10 is a schematic view of another exemplary microfluidic system for arranging objects, in accordance with aspects of the present disclosure.

FIG. 10 shows another exemplary microfluidic system 50' for arranging objects 54. System 50' may have any suitable combination of features described above for system 50 (see FIG. 1), such as a pump 110 to drive flow of carrier fluid 68 and objects 54, a partitioning structure 120, a detector 124 in communication with a detection zone 126, and the like.

The system also may include a channel structure 56 forming a reformatting zone 62. The reformatting zone may be created by a single channel 64 or by two or more channels of the channel structure, as described below in Section III. The reformatting zone may include an object-accessible region 76 and one or more object-excluding regions 77, which may be of different depth from one another, as described above for system 50 (see FIG. 3). Moreover, the reformatting zone may have a concentration section 78 in which a portion of carrier fluid 68 is moved from object-accessible region 76 to object-excluding regions 77, indicated by arrows at 80. Reformatting zone 62 also may have a dilution section 84 in which the portion of carrier fluid is reintroduced to object-accessible region 76 from object-excluding regions 77, indicated by arrows at 86.

However, reformatting zone 62 of system 50' may not be formed by an expanded region of channel 64 (compare with expanded region 98 of FIG. 1). Instead, channel 64, at the upstream end of reformatting zone 62, may be much wider than the diameter of objects 54 (e.g., more than 2, 3, 4, or 5 times the diameter of the objects), and may narrow toward the downstream end of reformatting zone 62. The objects may enter the reformatting zone spread out laterally from one another in a disordered arrangement (and not aligned). Objects 54 may be aligned with one another and placed into single file by tapered alignment region 118 of reformatting zone 62 (namely, object-accessible region 76 thereof) as the objects travel downstream through the reformatting zone. Alignment region 118 thus may be contiguous with each object-excluding region 77 (and one or more wings 82). The cross-sectional area for fluid flow may taper from the upstream end to the downstream end of the reformatting zone. Accordingly, in contrast to system 50, carrier fluid 68 may not be decelerated as it enters the reformatting zone.

III. Reformatting Zones

This section describes other exemplary channel geometries for reformatting zone 62 of system 50 and/or 50'; see FIGS. 11-18 (also see FIGS. 1-10). The outline convention for each pair of objects "A" and "B" in FIGS. 11-18 is as described above in Section II.

FIGS. 11-16 show three different geometries for reformatting zone 62, namely rectangular (FIGS. 11 and 12), round (FIGS. 13 and 14), and tapered (FIGS. 15 and 16). For each type of geometry, two embodiments are illustrated: one having uniform channel depth (FIGS. 11, 13, and 15), and the other having a deeper object-accessible region 76 and shallower object-excluding regions 77.

Figure 11:
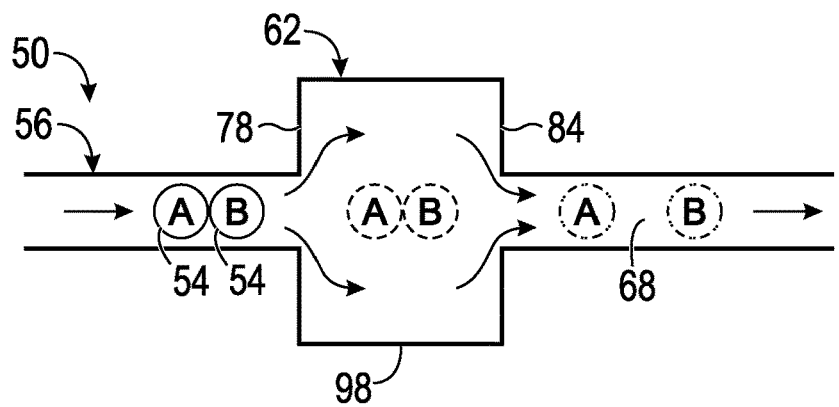
FIG. 11 is a view of an exemplary rectangular geometry for the reformatting zone of the microfluidic system of FIG. 1, with the reformatting zone having a uniform depth (and no object-excluding region), in accordance with aspects of the present disclosure.

FIG. 11 shows an exemplary rectangular geometry for reformatting zone 62 of system 50. The zone has an expanded region 98 to create upstream deceleration and downstream acceleration within the zone. However, the depth of reformatting zone 62 is uniform, such that carrier fluid 68 is not drained away from objects 54 efficiently.

Figure 12:
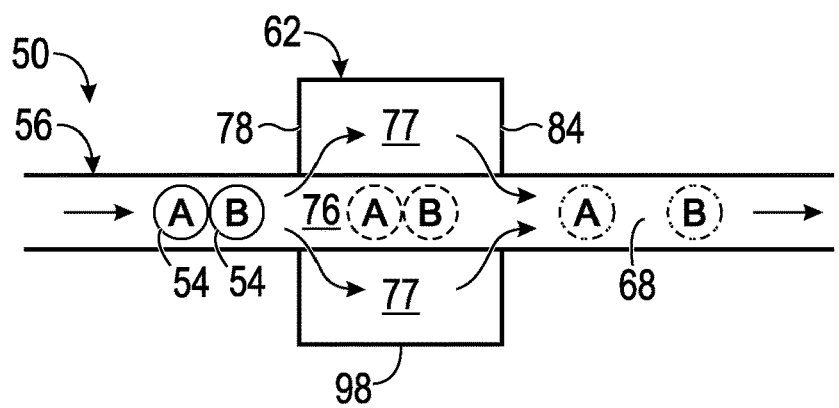
FIG. 12 is a view of another exemplary rectangular geometry for the reformatting zone of the microfluidic system of FIG. 1, with the reformatting zone having object-excluding regions of reduced depth to receive carrier fluid while restricting lateral travel of the objects, in accordance with aspects of the present disclosure.
Figure 13:
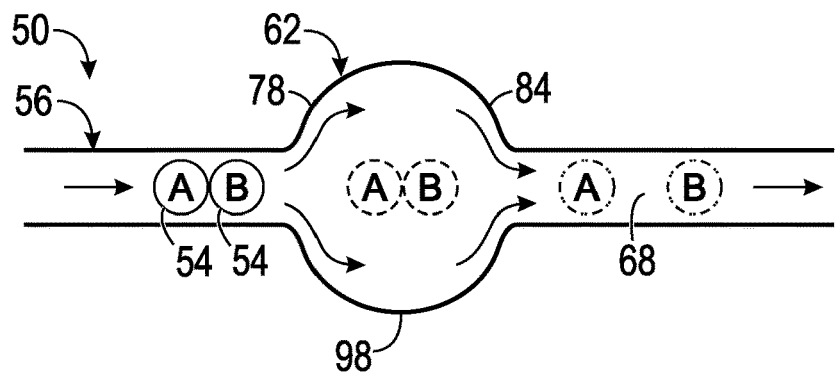
FIG. 13 is a view of an exemplary rounded geometry for the reformatting zone of the microfluidic system of FIG. 1, with the reformatting zone having a uniform depth (and no object-excluding region), in accordance with aspects of the present disclosure.
Figure 14:
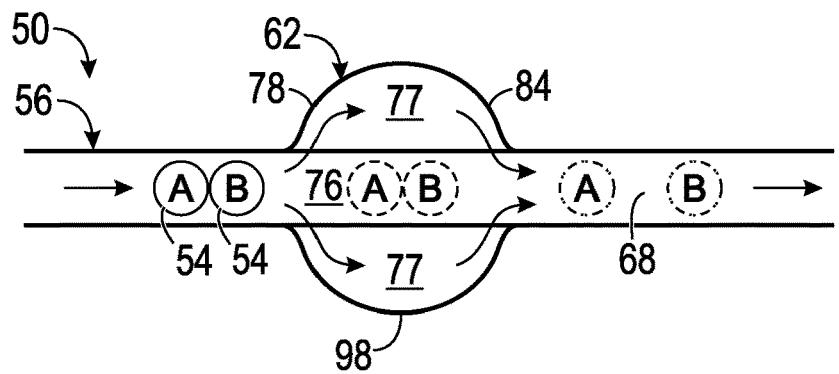
FIG. 14 is a view of another exemplary rounded geometry for the reformatting zone of the microfluidic system of FIG. 1, with the reformatting zone having object-excluding regions of reduced depth to receive carrier fluid while restricting lateral travel of the objects, in accordance with aspects of the present disclosure.

FIG. 12 shows another exemplary rectangular geometry for reformatting zone 62 of system 50. The perimeter of the zone has the same shape as in FIG. 11. However, the depth of zone 62 varies, as described above for system 50 of FIG. 1, to create object-accessible region 76 and object-excluding regions 77. The presence of object-excluding regions 77 allows the geometry of FIG. 12 to drain carrier fluid away from objects 54 much more efficiently than in FIG. 11, to produce a much greater concentration and dilution of objects by the zone. FIGS. 13 and 14 have the same general relation to one another as FIGS. 11 and 12, as do FIGS. 15 and 16.

FIG. 17 shows an exemplary branched geometry 130 for reformatting zone 62 of system 50. The zone has a primary channel 132 and one or more lateral by-pass channels 134. Each by-pass channel branches from primary channel 132 and rejoins the primary channel downstream. The primary channel forms object-accessible region 76, and the by-pass channels form object-excluding regions 77. Carrier fluid 68 may enter by-pass channels 134 in concentration section 78, to concentrate objects 54 in primary channel 132. Carrier fluid 68 may be reintroduced in dilution section 84 to dilute the objects. An inlet 136 of each by-pass channel 134, formed at the downstream end of an inflow channel 138, may be configured to exclude objects 54. For example, the inlet may have a width and/or a depth that is less than the diameter of the objects, and/or the inlet may include one or more pillars or other barriers to object entry. An outflow channel 140 may extend downstream from reformatting zone 62.

FIG. 18 shows another exemplary branched geometry 130 for reformatting zone 62 of system 50. The geometry of the reformatting zone of FIG. 18 is similar to that of FIG. 17 except that inflow channel 138 is much wider than the diameter of objects 54 (as in system 50' of FIG. 10). Also, primary channel 132 within zone 62 forms a tapered alignment region 118 (as in system 50' of FIG. 10).

IV. EXAMPLES

The following examples describe selected aspects and embodiments of microfluidic systems and methods for arranging objects. These aspects and embodiments are intended for illustration and should not limit the entire scope of the present disclosure.

Example 1

System and Method for Next Generation Sequencing

Figure 19:
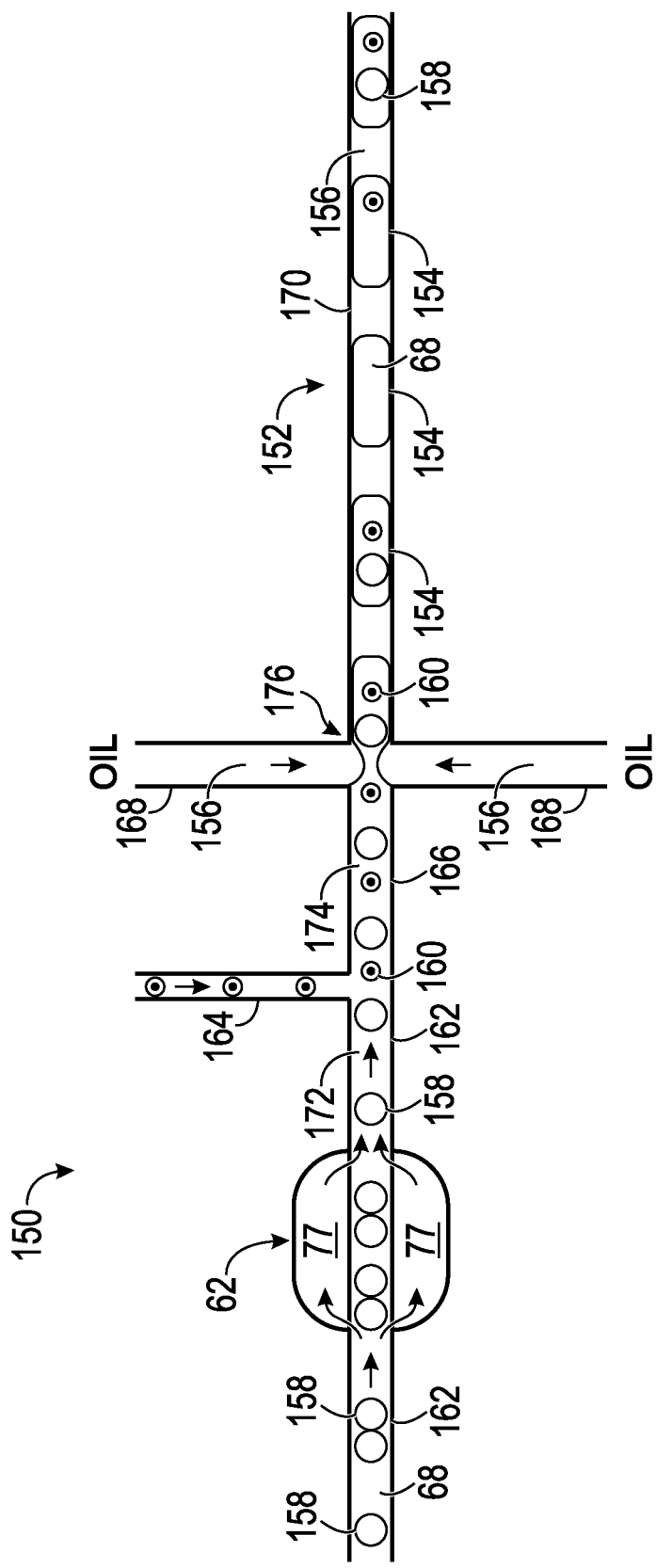
FIG. 19 is a schematic view of an exemplary embodiment of the system of FIG. 1 being used to form an emulsion, to enable next generation sequencing, in accordance with aspects of the present disclosure.

This example describes an exemplary system 150 and method for generating an emulsion 152 to enable next generation sequencing. The emulsion may include isolated volumes (droplets 154) of carrier fluid 68 encapsulated by an immiscible continuous phase liquid 156 (e.g., oil). Droplets 154 may contain beads 158 (as objects 54) and biological cells 160 at partial occupancy; see FIGS. 19 and 20. Beads 158 may carry oligonucleotides, which may be configured to function as primers and/or barcodes.

System has a channel structure including bead channel 162, at least one cell channel 164, at least one bead-and-cell channel 166, one or more oil channels 168, and a droplet channel 170. Bead channel 162 carries beads 158 through reformatting zone 62 to a junction with cell channel 164. Cells 160 are introduced to a bead-containing stream 172 at the junction to produce bead-and-cell-containing stream 174. Stream 174 travels to a channel junction 176 at which the stream may be segmented by at least one stream of continuous phase liquid 156 to generate droplets 154.

The goal is to have as many droplets as possible containing only one bead and only one cell, while minimizing the number of droplets containing two or more beads. With a Poisson distribution of the beads (no reformatting zone 62), the percentage of droplets containing one bead is kept relatively low, to avoid an unacceptably high fraction of droplets with two beads. Zone 62 permits a greater percentage of droplets (e.g., ~40%) to contain one bead, while fewer (e.g., ~5%) contain two beads. The percentage with three beads may be negligible.

Figure 20:
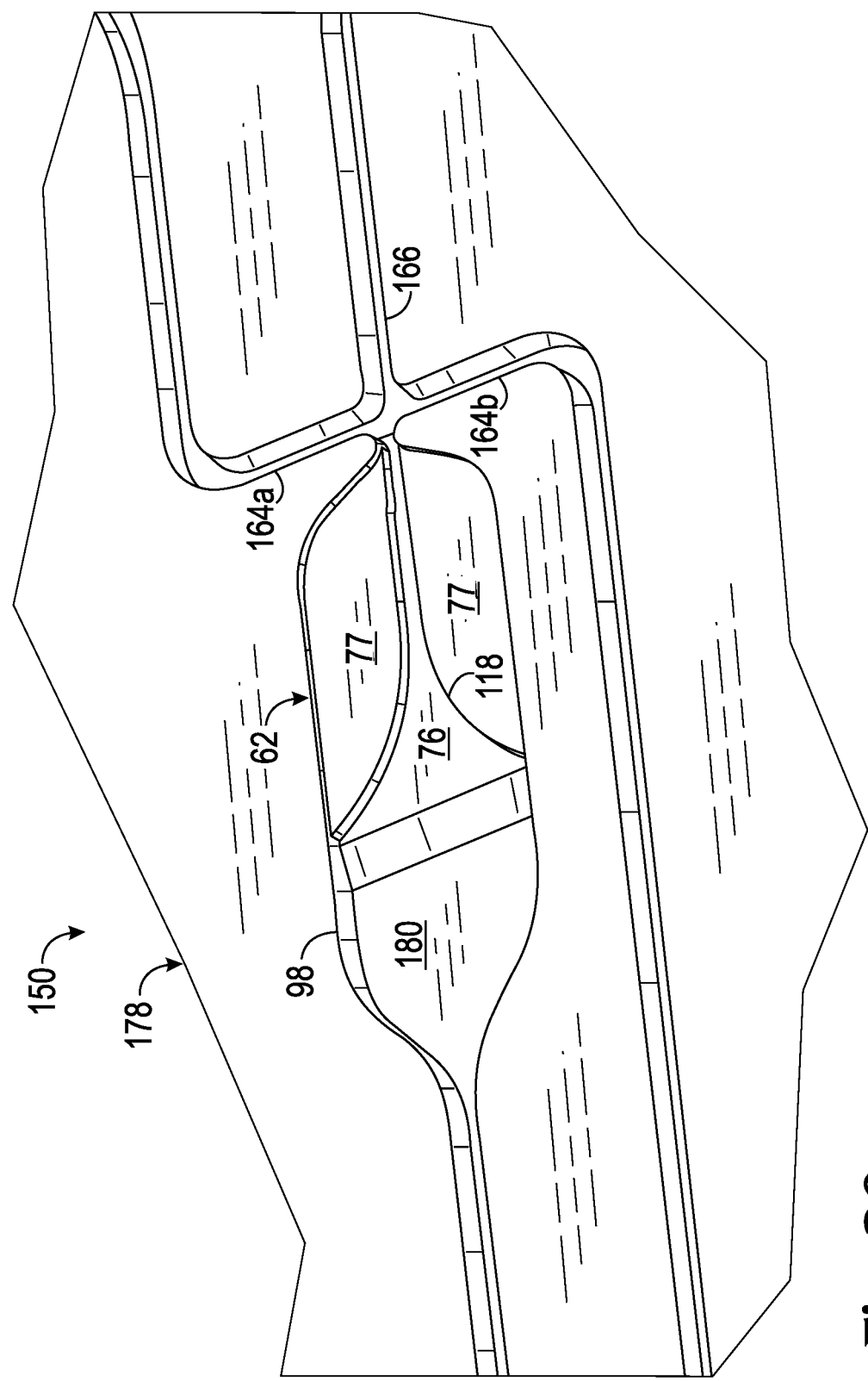
FIG. 20 is a fragmentary view of a bottom section of an embodiment of a channel-defining microfluidic device of the system of FIG. 19, taken around the reformatting zone of the device, in accordance with aspects of the present disclosure.

FIG. 20 shows a bottom section of a channel-defining microfluidic device 178 of an embodiment of system 150. Reformatting zone 62 has a wide expanded region 98 with a deep entry region 180 of uniform depth in which objects may accumulate. The expanded region becomes shallower to form a downstream portion of object-accessible region 76, and even shallower still to form lateral object-excluding regions 77. The downstream portion of object-accessible region 76 tapers to create alignment region 118 for the objects. A pair of cell channels 164a, 164b intersect the outlet of reformatting zone 62, to add biological cells to the outflowing stream of carrier fluid and beads. A resulting stream of carrier fluid transporting beads and biological cells travels along bead-and-cell channel 166.

Example 2

Selected Embodiments

This example describes selected embodiments of the present disclosure presented as a series of indexed paragraphs.

Paragraph A1. A method of arranging objects, the method comprising: (a) transporting a set of objects in carrier fluid along a microfluidic channel structure having a reformatting zone including an object-accessible region and at least one object-excluding region; (b) moving a portion of the carrier fluid from the object-accessible region to the object-excluding region(s) in an upstream section of the reformatting zone, to reduce a spacing of objects of the set; and (c) directing the portion of the carrier fluid into the object-accessible region from the object-excluding region(s) in a downstream section of the reformatting zone, to increase a spacing of objects of the set.

Paragraph A2. The method of paragraph A1, wherein at least one pair of objects of the set are in sufficiently close proximity to one another in the reformatting zone that the objects of the pair mutually obstruct a closer approach to one another encouraged by the step of moving.

Paragraph A3. The method of paragraph A1 or A2, wherein a spacing between a subset of the objects of the set that are closest together is increased disproportionately by the steps of moving and directing in combination.

Paragraph A4. The method of any of paragraphs A1 to A3, wherein objects of the set leave the reformatting zone in single file.

Paragraph A5. The method of any of paragraphs A1 to A4, further comprising a step of arranging objects of the set in single file.

Paragraph A6. The method of paragraph A5, wherein objects of the set are arranged in single file by an alignment region of the channel structure that does not overlap the upstream section.

Paragraph A7. The method of paragraph A5, wherein objects of the set are arranged in single file by an alignment region of the channel structure located in the upstream section.

Paragraph A8. The method of paragraph A6 or A7, wherein the alignment region tapers to a width that is less than twice an average diameter of the objects.

Paragraph A9. The method of any of paragraphs A1 to A8, wherein the object-accessible region is deeper than each object-excluding region of the at least one objection-excluding region.

Paragraph A10. The method of paragraph A9, wherein the object-excluding region has a depth that is less than an average diameter of the objects of the set.

Paragraph A11. The method of paragraph A9 or A10, wherein the object-accessible region and each object-excluding region of the at least one object-excluding region are formed by a same channel of the channel structure.

Paragraph A12. The method of paragraph A11, wherein each object-excluding region of the at least one object-excluding region is continuously contiguous with the object-accessible region between the upstream section and the downstream section.

Paragraph A13. The method of any of paragraphs A9 to A12, wherein the object-accessible region includes an object-accessible groove, and wherein the at least one object-excluding region includes one or more wings located adjacent the object-accessible groove.

Paragraph A14. The method of any of paragraphs A9 to A13, wherein the at least one object-excluding region includes a pair of object-excluding regions that are separated from one another by the object-accessible region, and optionally separated from one another only by the object-accessible region.

Paragraph A15. The method of any one of paragraphs A1 to A14, wherein the object-accessible region is formed by a primary channel of the channel structure, and wherein the step of moving includes a step of moving at least part of the portion of the carrier fluid to one or more by-pass channels defined by the channel structure.

Paragraph A16. The method of paragraph A15, wherein each by-pass channel branches from the primary channel in the upstream section and merges with the primary channel in downstream section.

Paragraph A17. The method of paragraph A15 or A16, wherein the one or more by-pass channels include a pair of by-pass channels, and wherein the primary channel is located between the pair of by-pass channels.

Paragraph A18. The method of any one of paragraphs A15 to A17, wherein each by-pass channel has an inlet configured to prevent entry of objects of the set into the by-pass channel.

Paragraph A19. The method of paragraph A18, wherein the inlet is sized to prevent entry of objects of the set into the by-pass channel.

Paragraph A20. The method of any one of paragraphs A1 to A19, wherein a plurality of objects of the set travel through the upstream section during the step of moving, and wherein only a subset of the plurality of objects move closer to an adjacent object of the set during the step of moving without being stopped by a periphery of the adjacent object.

Paragraph A21. The method of paragraph A20, wherein at least a pair of the plurality of objects do not move substantially closer to one another during the step of moving due to mutual obstruction.

Paragraph A22. The method of any one of paragraphs A1 to A21, wherein a plurality of objects of the set travel through the downstream section during the step of directing, wherein each object of the plurality of objects moves farther from each adjacent object of the plurality during the step of directing, Paragraph A23. The method of any one of paragraphs A1 to A22, wherein the steps of moving and directing, in combination, create substantially the same spacing for a subset of pairs of the objects that are closest to one another.

Paragraph A24. The method of paragraph A23, wherein objects of each of the pairs are spaced from one another by less than a threshold spacing before traveling through the formatting zone.

Paragraph A25. The method of any one of paragraphs A1 to A24, wherein the carrier fluid is an aqueous carrier fluid.

Paragraph A26. The method of any one of paragraphs A1 to A25, wherein the objects include liquid that is immiscible with the carrier fluid, and wherein, optionally, each of the objects is formed at least predominantly of liquid.

Paragraph A27. The method of any one of paragraphs A1 to A26, wherein the objects are selected from the group consisting of beads, droplets, and biological cells.

Paragraph A28. The method of any one of paragraphs A1 to A27, further comprising a step of partitioning a stream including the carrier fluid and carrying objects of the set at a position downstream of the downstream section to form isolated volumes.

Paragraph A29. The method of paragraph A28, wherein each isolated volume of a majority of the isolated volumes contains none or only one of the objects of the set.

Paragraph A30. The method of paragraph A28 or A29, wherein the step of partitioning includes a step of encapsulating the isolated volumes with a liquid that is immiscible with the carrier fluid.

Paragraph A31. The method of any one of paragraphs A28 to A30, wherein the step of partitioning includes a step of forming droplets.

Paragraph A32. The method of any one of paragraphs A28 to A31, wherein the objects are beads, further comprising a step of adding biological cells to the carrier fluid.

Paragraph A33. The method of paragraph A32, wherein each isolated volume of a plurality of the isolated volumes contains only one of the beads and only one biological cell.

Paragraph A34. The method of any one of paragraphs A1 to A33, further comprising a step of moving one or more of the objects of the set through a detection zone downstream of the downstream section, and a step of detecting a signal from the detection zone.

Paragraph A35. The method of paragraph A34, wherein the step of detecting a signal includes a step of detecting light.

Paragraph B1. A method of altering the spacing of a stream of objects, the method comprising: (a) transporting objects of the object stream in carrier fluid along an object-accessible flow path, the flow path being defined by a microfluidic channel structure and extending through a reformatting zone including an upstream section and a downstream section; (b) moving a portion of the carrier fluid out of the flow path in the upstream section such that objects within the object stream move closer to one another; and (c) directing the portion of the carrier fluid into the flow path in the downstream section to increase a distance between objects within the object stream.

Paragraph B2. The method of paragraph B1, wherein the object stream has a more uniform spacing of objects downstream of the downstream section compared to upstream of the upstream section, and/or wherein a distance between object pairs of the object stream that are closest together upstream of the upstream section is increased disproportionately by the steps of moving and directing in combination.

Paragraph B3. The method of paragraph B1 or paragraph B2, wherein the channel structure includes an object-accessible groove and at least one object-excluding wing located adjacent the groove.

Paragraph B4. The method of paragraph B3, wherein the step of moving includes a step of moving the portion of the carrier fluid from a deeper region to at least one shallower region of the channel structure.

Paragraph B5. The method of paragraph B4, wherein the step of moving includes a step of moving the portion of the carrier fluid to a pair of shallower regions of the channel structure that are separated from one another by a deeper, object-accessible groove.

Paragraph B6. The method of paragraph B4 or B5, wherein the step of moving includes a step of moving the portion of the carrier fluid to at least one shallower region having a depth that is less than a diameter of the objects, such that a majority of objects of the object stream are excluded from the at least one shallower region.

Paragraph B7. The method of any one of paragraphs B1 to B6, wherein the step of moving includes a step of moving the portion of the carrier fluid from a primary channel to one or more by-pass channels defined by the channel structure.

Paragraph B8. The method of paragraph B7, wherein the channel structure has a primary channel, and wherein each by-pass channel branches from the primary channel in the upstream section and merges with the primary channel in the downstream section.

Paragraph B9. The method of paragraph B8, wherein the one or more by-pass channels include a pair of by-pass channels.

Paragraph B10. The method of any one of paragraphs B7 to B9, wherein each by-pass channel has an inlet configured to prevent entry of objects of the object stream into the by-pass channel.

Paragraph B11. The method of paragraph B10, wherein the inlet is sized to prevent entry of objects of the object stream into the by-pass channel.

Paragraph B12. The method of any of paragraphs B1 to B11, wherein a plurality of the objects of the object stream travel through the upstream section during the step of moving, and wherein only a subset of the plurality of objects move closer to an adjacent object of the object stream during the step of moving until closer approach is obstructed by a periphery of the adjacent object.

Paragraph B13. The method of any of paragraphs B1 to B12, wherein at least a pair of the plurality of objects do not move substantially closer to one another during the step of moving due to mutual obstruction.

Paragraph B14. The method of any one of paragraphs B1 to B13, wherein a plurality of the objects travel through the downstream section during the step of directing, and wherein each object of the plurality of objects moves farther from each adjacent object of the object stream during the step of directing.

Paragraph B15. The method of any one of paragraphs B1 to B14, wherein the carrier fluid is an aqueous carrier fluid.

Paragraph B16. The method of any one of paragraphs B1 to B15, wherein the objects are formed at least predominantly of liquid that is immiscible with the carrier fluid.

Paragraph B17. The method of any one of paragraphs B1 to B16, wherein the objects are selected from the group consisting of beads, droplets, and biological cells.

Paragraph B18. The method of any one of paragraphs B1 to B17, further comprising a step of forming partitions from a stream including the carrier fluid and carrying a plurality of the objects at a position of the channel structure downstream of the downstream section.

Paragraph B19. The method of paragraph B18, wherein each partition of a majority of the partitions contains none or only one of the objects.

Paragraph B20. The method of paragraph B18 or B19, wherein the step of forming partitions includes a step of encapsulating volumes of the stream with an immiscible liquid.

Paragraph B21. The method of any one of paragraphs B18 to B20, wherein the step of forming partitions includes a step of forming droplets.

Paragraph B22. The method of any one of paragraphs B18 to B21, wherein the objects are beads, further comprising a step of adding biological cells to the carrier fluid.

Paragraph B23. The method of paragraph B22, wherein each partition of a plurality of the partitions contains only one of the beads and only one biological cell.

Paragraph B24. The method of any one of paragraphs B1 to B23, further comprising a step of passing one or more of the objects through a detection zone downstream of the downstream section, and a step of detecting a signal from the detection zone.

Paragraph B25. The method of paragraph B24, wherein the step of detecting a signal includes a step of detecting light.

Paragraph C1. A method of altering the spacing of a stream of objects, the method comprising: (a) transporting objects of the object stream in carrier fluid along a microfluidic channel structure having a deceleration region upstream of an acceleration region; (b) slowing down objects within the object stream at the deceleration region such that at least a subset of such objects are moved closer to one another; and (c) speeding up objects of the object stream at the acceleration region to increase a distance between such objects; wherein the object stream has a lower incidence of closely-spaced pairs of the objects downstream of the acceleration region compared to upstream of the deceleration region.

Paragraph C2. The method of paragraph C1, further comprising any one or combination of the limitations from paragraphs A1 to A35 and B1 to B25.

Paragraph D1. A method of altering the spacing of a stream of objects, the method comprising: (a) transporting the objects of the object stream in carrier fluid along a microfluidic channel structure having an inflow region, an outflow region, and an expanded region extending from the inflow region to the outflow region, wherein the expanded region has a greater cross-sectional area for fluid flow than the inflow region and the outflow region; (b) moving objects of the object stream from the inflow region to the expanded region such that at least a subset of such objects are moved closer to one another; and (c) passing objects of the object stream from the expanded region to the outflow region to increase a distance between such objects.

Paragraph E1. A system for arranging a set of objects, comprising: (a) a microfluidic channel structure having a reformatting zone including an object-accessible region and at least one object-excluding region; and (b) at least one source of positive/negative pressure operatively connected to the channel structure and configured to form a stream of carrier fluid transporting objects of the set in the channel structure; wherein the channel structure is configured such that a portion of the carrier fluid is moved from the object-accessible region to the at least one object-excluding region in an upstream section of the reformatting zone, to reduce a spacing between objects of the set, and such that the portion of the carrier fluid is directed into the object-accessible region from the at least one object-excluding region in a downstream section of the reformatting zone, to increase a spacing between objects of the set.

Paragraph E2. The system of paragraph E1, further comprising any one or combination of the limitations from paragraphs A1 to A35, B1 to B25, C1 to C2, and D1.

Paragraph F1. A system for altering the spacing of a stream of objects, comprising: (a) a microfluidic channel structure having an inflow region, an outflow region, and an expanded region extending from the inflow region to the outflow region, wherein the expanded region has a greater cross-sectional area for fluid flow than the inflow region and the outflow region; (b) a source of carrier fluid and objects in communication with the inflow region of the channel structure; and (c) at least one source of positive/negative pressure operatively connected to the channel structure and configured to form a stream of carrier fluid transporting a stream of objects, such that objects of the object stream pass from the inflow region to the expanded region and at least a subset of such objects are moved closer to one another, such that objects of the object stream are directed from the expanded region to the outflow region to increase a distance between such objects, and such that the object stream has a more uniform spacing of the objects downstream of the expanded region compared to upstream of the expanded region.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated. Finally, the present disclosure incorporates material by reference. If any ambiguity or conflict in the meaning of a term results from this incorporation by reference, the literal contents of the application govern construction of the term.

We claim:

1. A method of arranging objects, the method comprising:
transporting a set of objects in carrier fluid along a microfluidic channel structure having a reformatting zone including an object-accessible region and at least one object-excluding region;
moving a portion of the carrier fluid from the object-accessible region to the at least one object-excluding region in an upstream section of the reformatting zone, to reduce a spacing of objects of the set in the upstream section; and
directing the portion of the carrier fluid into the object-accessible region from the at least one object-excluding region in a downstream section of the reformatting zone, to increase a spacing of objects of the set in, and/or downstream of, the downstream section.

2. The method of claim 1, wherein at least one pair of objects of the set are in sufficiently close proximity to one another in the reformatting zone that the objects of the at least one pair mutually obstruct a closer approach to one another encouraged by the step of moving.

3. The method of claim 1, wherein a spacing between a subset of the objects of the set that are closest together is increased disproportionately by the steps of moving and directing in combination.

4. The method of claim 1, wherein objects of the set leave the reformatting zone in single file.

5. The method of claim 1, wherein the reformatting zone has an outlet, further comprising arranging objects of the set in single file in the channel structure upstream of the outlet of the reformatting zone.

6. The method of claim 5, wherein objects of the set are arranged in single file by an alignment region of the channel structure located in the upstream section.

7. The method of claim 5, wherein objects of the set are arranged in single file by an alignment region of the channel structure that tapers from the upstream section to the downstream section of the reformatting zone.

8. The method of claim 7, wherein the alignment region tapers to a width that is less than twice an average diameter of the objects.

9. The method of claim 1, wherein the object-accessible region is deeper than each object-excluding region of the at least one object-excluding region.

10. The method of claim 9, wherein the at least one object-excluding region has a depth that is less than an average diameter of the objects of the set.

11. The method of claim 9, wherein the object-accessible region and each object-excluding region of the at least one object-excluding region are formed by a same channel of the channel structure.

12. The method of claim 11, wherein each object-excluding region of the at least one object-excluding region is continuously contiguous with the object-accessible region between the upstream section and the downstream section.

13. The method of claim 9, wherein the object-accessible region includes an object-accessible groove, and wherein the at least one object-excluding region includes one or more wings located adjacent the object-accessible groove.

14. The method of claim 9, wherein the at least one object-excluding region includes a pair of object-excluding regions that are separated from one another by the object-accessible region.

15. The method of claim 1, wherein the object-accessible region is formed by a primary channel of the channel structure, wherein the at least one object-excluding region includes one or more by-pass channels defined by the channel structure, and wherein the step of moving includes a step of moving at least part of the portion of the carrier fluid to the one or more by-pass channels.

16. The method of claim 1, wherein the objects are selected from the group consisting of beads, droplets, and biological cells.

17. The method of claim 1, further comprising partitioning a stream including the carrier fluid and carrying objects of the set at a position downstream of the downstream section to form isolated volumes, wherein partitioning includes encapsulating the isolated volumes with a liquid that is immiscible with the carrier fluid.

18. The method of claim 17, wherein the objects include biological cells, wherein the stream includes beads, and wherein each isolated volume of a plurality of the isolated volumes contains only one of the beads and only one of the biological cells.

19. A system for arranging a set of objects, comprising:
a microfluidic channel structure having a reformatting zone including an object-accessible region and at least one object-excluding region; and
at least one source of positive/negative pressure operatively connected to the channel structure and configured to form a stream of carrier fluid transporting objects of the set in the channel structure;
wherein the channel structure is configured such that a portion of the carrier fluid is moved from the object-accessible region to the at least one object-excluding region in an upstream section of the reformatting zone, to reduce a spacing between objects of the set in the upstream section, and such that the portion of the carrier fluid is directed into the object-accessible region from the at least one object-excluding region in a downstream section of the reformatting zone, to increase a spacing between objects of the set in, and/or downstream of, the downstream section.

* * * * *